US010745327B2

(12) United States Patent
Dent et al.

(10) Patent No.: US 10,745,327 B2
(45) Date of Patent: Aug. 18, 2020

(54) PLANT INOCULATION METHOD (71) Applicant: AZOTIC TECHNOLOGIES LTD, Chorley Lancashire (GB)

(72) Inventors: David Dent, Fleet Hampshire (GB); Ian Clarke, Nottingham Nottinghamshire (GB)

(73) Assignee: Azotic Technologies LTD, Lancashire (GB)

( * ) Notice: Subject to any disclaimer, the term of this patent is extended or adjusted under 35 U.S.C. 154(b) by 101 days.

(21) Appl. No.: 15/326,996

(22) PCT Filed: Jul. 28, 2015

(86) PCT No.: PCT/GB2015/052170
§ 371 (c)(1),
(2) Date: Jan. 17, 2017

(87) PCT Pub. No.: WO2016/016629
PCT Pub. Date: Feb. 4, 2016

(65) Prior Publication Data
US 2017/0240480 A1   Aug. 24, 2017

(30) Foreign Application Priority Data

Jul. 28, 2014  (GB) .................................. 1413333.4

(51) Int. Cl.
*C05F 11/08*  (2006.01)
*C12N 1/20*  (2006.01)
(Continued)

(52) U.S. Cl.
CPC .............. *C05F 11/08* (2013.01); *A01N 63/10* (2020.01); *C05G 3/70* (2020.02); *C05G 5/23* (2020.02);
(Continued)

(58) Field of Classification Search
None
See application file for complete search history.

(56) References Cited

U.S. PATENT DOCUMENTS

| 5,664,368 A | 9/1997 | Sandor | |
| 2011/0225679 A1* | 9/2011 | Vessey | .................... C05F 11/08 800/298 |

(Continued)

FOREIGN PATENT DOCUMENTS

| WO | 02/058466 A2 | 8/2002 |
| WO | 03/020014 A2 | 3/2003 |

(Continued)

OTHER PUBLICATIONS

Arencibia et al., "Gluconacetobacter diazotrophicus Elicits a Sugarcane Defense Response Against a Pathogenic Bacteria Xanthomonas albilineans", Plant Signaling & Behavior, 2006, pp. 265-273, vol. 1, No. 5.

(Continued)

*Primary Examiner* — Wayne A Langel (57) ABSTRACT

A method for inoculating a plant with a nitrogen-fixing bacteria such as *Gluconacetobacter diazotrophicus*, said method comprising administering the nitrogen-fixing bacteria to a wound of a growing plant, for example to recently cut grass. Inoculation in this manner leads to enhanced growth characteristics including increased greenness of grass. Novel compositions suitable for use in the method are also described and claimed, together with kits for producing these.

17 Claims, 4 Drawing Sheets

Specification includes a Sequence Listing.

US 10,745,327 B2

Page 2

(51) Int. Cl.

| | |
|---|---|
| *C12R 1/02* | (2006.01) |
| *C12R 1/01* | (2006.01) |
| *A01N 63/10* | (2020.01) |
| *C05G 3/70* | (2020.01) |
| *C05G 5/27* | (2020.01) |
| *C05G 5/23* | (2020.01) |

(52) U.S. Cl.
CPC ............... *C05G 5/27* (2020.02); *C12N 1/20* (2013.01); *C12R 1/01* (2013.01); *C12R 1/02* (2013.01)

(56) References Cited

U.S. PATENT DOCUMENTS

| | | | | |
|---|---|---|---|---|
| 2013/0145805 | A1* | 6/2013 | Olson | C05D 9/00 71/6 |
| 2014/0230504 | A1* | 8/2014 | Finlayson | C05F 11/02 71/6 |

FOREIGN PATENT DOCUMENTS

| | | | |
|---|---|---|---|
| WO | 2010/022517 | A1 | 3/2010 |
| WO | 2011/144741 | A2 | 11/2011 |
| WO | 2016/016629 | A1 | 2/2016 |

OTHER PUBLICATIONS

Badar et al., "Seed Physiology of Some Pulses and Cereals Under the Influence of Acacia Arabica Gum", Recent Research in Science and Technology, 2011, pp. 06-07, vol. 3, No. 5.

Boddey et al., "Endophytic nitrogen fixation in sugarcane: present knowledge and future applications", Plant and Soil, 2003, pp. 139-149, vol. 252, No. 1.

Cavalcante et al., "A new acid-tolerant nitrogen-fixing bacterium associated with sugarcane", Plant and Soil, 1988, pp. 23-31, vol. 108, No. 1.

Cocking et al., "Intracellular Colonization of Roots of Arabidopsis and Crop Plants by Gluconacetobacter Diazotrophicus", In Vitro Cellular and Developmental Biology—Plant, 2006, pp. 74-82, vol. 42, No. 1.

Cojho et al., "Interactions of Acetobacter diazotrophicus with an amylolytic yeast in nitrogen-free batch culture", EMS Microbiology Letters, 1993, pp. 341-346, vol. 106.

Eskin et al., "Research Progress and Perspectives of Nitrogen Fixing Bacterium, Gluconacetobacter diazotrophicus, in Monocot Plants", International Journal of Agronomy, 2014, 13 pgs., vol. 60, No. 10.

Fang et al., "Interaction of Gum Arabic with Fatty Acid Studied Using Electron Paramagnetic Resonance", Biomacromolecules, 2010, pp. 1398-1405, vol. 11, No. 5.

Fuentes-Ramirez et al., "Colonization of sugarcane by Acetobacter diazotrophicus is inhibited by high N-fertilization", FEMS Microbiology Ecology, 1999, pp. 117-128, vol. 29.

Gillis et al., "*Acetobacter diazotrophicus* sp. nov., a Nitrogen-Fixing Acetic Acid Bacterium Associated with Sugarcane", International Journal of Systematic Bacteriology, 1989, pp. 361-364, vol. 39, No. 3.

International Search Report and Written Opinion from International Application No. PCT/GB2015/052170, dated Oct. 20, 2015; 12 pgs.

James et al., "Further observations on the interaction between sugar cane and Gluconacetobacter diazotrophicus under laboratory and greenhouse conditions", Journal of Experimental Botany, 2001, pp. 747-760, vol. 52, No. 357.

Nita et al., "Liquid formulations of Acetobacter diazotrophicus L1 and Herbaspirillum seropedicae J24 and their field trials on wheat", International Journal of Environmental Sciences, 2012, pp. 1116-1129, vol. 3, No. 3.

Schultz et al., "Inoculation of Sugarcane With Diazotrophic Bacteria", R. Bras. Ci. Solo, 2014, pp. 407-414, vol. 38.

Sevilla et al., "Comparison of Benefit to Sugarcane Plant Growth and 15N2 Incorporation Following Inoculation of Sterile Plants with Acetobacter diazotrophicus Wild-Type and Nif-Mutant Strains", Molecular Plant-Microbe Interactions, 2001, pp. 358-366, vol. 14, No. 3.

Tejera et al., "Nitrogen compounds in the apoplastic sap of sugarcane stem: Some implications in the association with endophytes", Journal of Plant Physiology, 2006, pp. 80-85, vol. 163.

Tian et al., "Colonization of the nitrogen-fixing bacterium Gluconacetobacter diazotrophicus in a large number of Canadian corn plants", Canadian Journal of Plant Science, 2009, pp. 1009-1016, vol. 89, No. 6.

Office Action from related European Patent Application No. 15754282.0, dated Sep. 5, 2018; 6 pgs.

Gagne et al., "Xylem-residing bacteria in alfalfa roots", Canadian Journal of Microbiology, 1987, pp. 996-1000, vol. 33, No. 11.

Karthikeyan et al., "Efficacy of Azotobacter chroococcum in Rooting and Growth of Eucalyptus camaldulensis Stem Cuttings", Research Journal of Microbiology, 2011, pp. 618-624, vol. 6, No. 7.

Taghavi et al., "Genome Survey and Characterization of Endophytic Bacteria Exhibiting a Beneficial Effect on Growth and Development of Poplar Trees", Applied and Environmental Microbiology, 2009, pp. 748-757, vol. 75, No. 3.

First Office Action relating to Chinese Patent Application No. 201580041250.2, dated Oct. 21, 2019; 14 pgs.

Exam Report relating to European Patent Application No. 15754282.0, dated Aug. 1, 2019; 8 pgs.

Examination report No. 3 relating to Australian Patent Application No. 2015295037, dated Oct. 4, 2019; 6 pgs.

Daniel et al., "Effect of Polymeric Additives, Adjuvants, Surfactants on Survival, Stability and Plant Growth Promoting Ability of Liquid Bioinoculants," Journal of Plant Physiology & Pathology, 2013, pp. 1-5, vol. 1, No. 2.

Feng-Jiao et al., "Inoculation of entophytic diazotrophs on hybrid Bermudagrass," Pratacultural Science, 2013, pp. 1953-1959, vol. 30, No. 12.

Hossain et al., "Interactions between Starch and Surfactants by Ternary Phase Diagram," Canadian Journal on Scientific and Industrial Research, 2012, pp. 246-255, vol. 3, No. 4.

Original Deposit Receipt for Accession No. IMI CC No. 504958, under the Budapest Treaty, received on Jun. 17, 2015.

Original Deposit Receipt for Accession No. IMI CC No. 504998, under the Budapest Treaty, received on Jul. 28, 2015.

\* cited by examiner

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 1
tagtggcgga cgggtgagta acg                                    23

<210> SEQ ID NO 2
<211> LENGTH: 22
<212> TYPE: DNA
```

```
<213> ORGANISM: Artificial Sequence
<220> FEATURE:
<223> OTHER INFORMATION: SYNTHESIZED

<400> SEQUENCE: 2
ccttgcggga aacagccatc tc                                              22

<210> SEQ ID NO 3
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 3
tgagtaacgc gtagggatct g                                               21

<210> SEQ ID NO 4
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 4
ggaaacagcc atctctgact g                                               21
```

PLANT INOCULATION METHOD

FIELD OF THE INVENTION

The present invention relates to a method for inoculating plants with a nitrogen-fixing bacteria and to compositions and kits suitable for use in that method.

BACKGROUND TO THE INVENTION

The nitrogen-fixing bacterium *Gluconacetobacter diazotrophicus*, previously known as *Acetobacter diazotrophicus* (Gillis, M. et al. Int. J. Syst. Bacteriol. 39:361-364; 1989), was originally isolated from within sugarcane roots and stems (Cavalcante, V. A., et al. (1988) *Plant Soil* Vol. 108, p. 23-31). It has been demonstrated by $^{15}N_2$ incorporation that *G. diazotrophicus* fixes nitrogen inside sugarcane plants (Sevilla, M. et al. Mol. Plant Microbe Interact. 14:358-366; 2001; Boddey, R. M. et al. Plant Soil 252:139-149; 2003) and that it has a capability to excrete almost half of the fixed nitrogen in a form that is potentially available to plants (Cojho, E. H et al. Fed. Eur. Microbiol. Soc. Microbiol. Lett. 106:341-346; 1993). The bacterium invades between cells of sugarcane root meristems and at emergence points of lateral roots colonizing intercellularly, and also in the xylem, without nodulation (James, E. K. et al. J. Exp. Bot. 52:747-760; 2001). The conditions under which intracellular colonisation of Gd could occur enabling non-nodular endosymbiotic nitrogen fixation has been demonstrated (EP-B-1422997 and Cocking, E. C., et al. (2006) In *Vitro Cellular and Developmental Biology—Plant* Vol. 42, No. 1, p 74-82). In particular, the bacteria are administered to the growth medium of the plant as the plant grows on germination or within 7 days thereof.

WO2011/144741 suggests that bacteria such as Gd, may be injected into stems of sugarcane to enhance nitrogen-fixation. Clearly such a technique is not one which could be applied in any large scale agricultural operation.

The applicants have found that growing plants can be successfully inoculated with nitrogen fixing bacteria.

SUMMARY OF THE INVENTION

According to the present invention there is provided a method for inoculating a plant with a nitrogen-fixing bacteria, said method comprising administering the nitrogen-fixing bacteria to a wound of a growing plant.

DETAILED DESCRIPTION OF THE INVENTION

It has been found that when applied to a wound in particular to the surface of a wound in plant tissue, subsequent plant growth is enhanced. For example the biomass or yield may be enhanced and/or, the number of flowers may be increased. This may be due to colonisation of the plant tissue by the nitrogen-fixing bacteria in a similar manner to that described for instance in EP-B-1422997, although the fact that this may occur when applied in this manner is surprising. The nitrogen-fixing bacteria colonised within the plant tissue may provide a source of intracellular nitrogen that enhances plant growth. Thus the method of the invention provides a useful means of administering a plant growth enhancing treatment to growing plants.

The nitrogen-fixing bacteria should suitably be one which may become intracellularly located within a plant cell. In a particular embodiment, this is the intracellulary colonising symbiotic nitrogen-fixing bacteria *Gluconacetobacter diazotrophicus* (Gd), for instance *Gluconacetobacter diazotrophicus* strain IMI 504998 (formerly IMI 501986) or IMI 504958 (formerly IMI 504853), both being deposited at CABI (UK). IMI 501986 is an accession number for a deposit with CABI that was made on 21 Sep. 2012. There was then a conversion on 28 Jul. 2015 to a deposit under the Budapest Treaty, which was given the new accession number of 504998 . Such strains are novel and form a further aspect of the invention. Alternatively, the nitrogen-fixing bacteria may be a species of *Herbaspirillum*. Other nitrogen fixing bacteria include *Azotobacter, Beijerinckia, Clostridium, Rhizobium, Klebsiella* and *Spirillum lipoferum*.

In a particular embodiment, the nitrogen-fixing bacteria is administered together or in combination with a strain of *Terribacillus*, as described in the applicants co-pending International patent application which claims priority from British Patent Application No. 1400840.3. The applicants have found that such a strain may enhance the activity of the nitrogen-fixing bacteria. Suitable strains of *Terribacillus* include *Terribacillus saccharophilus, Terribacillus halophilus, Terribacillus goriensis* or *Terribacillus aidingensis* but in particular is a strain of *Terribacillus saccharophilus*. The *Terribacillus Terribacillus* either separately or in admixture with the nitrogen-fixing bacteria. The *Terribacillus* may be in intimate admixture with the nitrogen-fixing bacteria, (and indeed, IMI501986 (now IMI 504998) has been classified as a consortium of Gd and *Terribacillus*,) or it may be administered in a co-culture, or mixed culture form.

The wound may be a result of accidental or natural damage, whereupon the additional nitrogen availability may facilitate repair growth. However, in a particular embodiment, the wound is the result of damage caused by actions such as mowing (amenity grass), cutting (silage and hay crops), ratooning (banana, pineapple, sugarcane, sorghum, rice, pigeonpea, cotton, Abaca, Ramie), pruning (fruit trees, vines), consumption by livestock or by harvesting. Other processes, such as harrowing, in which plants may be inadvertently or incompletely damaged, may not be suitable in some instances. In particular, the wound will be found in an 'above-ground' part of the plant, such as leaves or stems.

Therefore, the method of the invention may further comprise a preliminary step of inflicting 'damage' on the plant, in particular by mowing, cutting, rationing, pruning or by harvesting. The nitrogen-fixing bacteria is suitably applied within a relatively short time period of carrying out such actions, for instance, within 48 hours, for instance within 24 hours, such as within 10 hours and suitably within 1-2 hours of damage being inflicted on the plant.

Delivery of the bacteria is achieved by application of a suitable formulation to the wound area, in particular to the surface of the wound, in the form of a composition. The composition may be in the form of a liquid, gel, paste which may be applied directly or in diluted form, or it may be in the form of a solid composition such as a powder or granule composition that will be dissolved in liquid such as water before use. In solid compositions, the bacteria will generally be used in dried form, for example in freeze-dried form, which are reconstitutable on addition of water. If desired, the bacteria may be microencapsulated using methods known in the art, in order to maintain high viability and stability of the bacteria.

In a particular embodiment, the composition is in a form suitable for spraying on the plants and thus will comprise a concentrate for dilution which may be in the form of a liquid or solid, in particular in the form of a liquid, or it may comprise a dilute aqueous composition that may be sprayed directly. Alternatively, the composition may be one in which the wound surface of a plant may be immersed by dipping for instance.

The amount of nitrogen-fixing bacteria that is administered in any particular case will vary depending upon factors such as the type of seed being treated, the particular strain of nitrogen-fixing bacteria used, the level of germination enhancement required and the method of administration, as well as the effect required. Typically however, a solution containing from 1 to $1\times10^7$ bacteria per millilitre of composition applied, for example from $10$-$10^3$ bacteria per millilitre of composition for instance from 50-200 bacteria per millilitre of composition such as 100 bacteria per millilitre of composition is administered to the wounds of a plant. Such a solution may be obtained by culturing the bacteria to a readily detectable level for example by examining the optical density and then diluting the solution accordingly.

The applicants have found for instance that, in the case of certain bacteria, the effects on a property such as biomass, is affected by the amount of bacteria applied in a dose dependent manner. This means that different doses may be administered depending upon the aim of the treatment. In the case of grasses for instance, it may be required that biomass is maximised in pasture grass, whereas in amenity or turf grass, slow growth may be preferable. In such cases, the amount of bacteria administered will be selected to provide optimum biomass production for the target grass species, as exemplified below.

In a particular embodiment, the composition further comprises a nutrient for the nitrogen-fixing bacteria, for example the composition may comprise 3% w/v sucrose as described in EP-B-1422997.

The nitrogen-fixing bacteria may be the sole active component of the composition or it may be combined with additional agrochemically active components such as insecticides, fungicides or plant growth regulators as required.

The composition may further comprise additives or excipients such as thickening agents, dispersants, diluents, humectants, solid carriers etc. as are known in the art.

In a particular embodiment, the composition further comprises a polysaccharide or an agriculturally acceptable surfactant or a combination of these.

In a particular embodiment, the composition further comprises an agriculturally acceptable surfactant. The presence of a surfactant ensures that the composition is able to flow relatively freely over the entire surface of the wounds to facilitate entry of the nitrogen-fixing bacteria.

Suitable surfactants or detergents include non-ionic detergents such as those sold under the trade name 'Tween'®, for example Tween 80.

Tween 80 is a non-ionic detergent; 70% composed of the fatty acid oleic acid and the remainder a combination of linoleic, palmitic and stearic acids. The pH of a 1% solution is in the range of from 5.5-7.2. It is widely used for emulsifying and dispersing substances in medicinal and food products. It has little or no activity as an anti-bacterial agent (Dawson et al. (1986) Data for Biochemical Research, 3rd ed., Oxford University Press (New York, N.Y.: 1986), p. 289).

The amount of surfactant administered to the plant wound should be sufficient to produce an enhanced plant growth effect when in combination with the nitrogen-fixing bacteria (and optionally also a polysaccharide as described further below). This will vary depending upon the various factors such as the particular surfactant, the type of plant being treated, the nature of the wound, the particular strain of nitrogen-fixing bacteria employed and the method of administration. However, typically, a composition comprising from 0.0005 to 10% v/v, such as from 0.0005 to 0.5% v/v, for instance from 0.0005 to 1% v/v, including from 0.0005 to 0.2% v/v for example from 0.0005 to 0.15% v/v such as about 0.1% v/v.

In a further embodiment, the composition comprises a polysaccharide. Suitable polysaccharides for use in the composition include hydrocolloid polysaccharides derived from plant, animal or microbial sources.

In particular, these include exudate gum polysaccharides such as gum Arabic, gum ghatti, gum karaya and gum tragacanth, cellulosic derivatives such as carboxymethylcellulose, methylcellulose, hydroxypropyl cellulose, hydroxypropyl methylcellulose or microcrystalline cellulose, starches and derivatives including, for instance corn starch, tapioca starch, potato starch, rice starch, wheat starch, and modified versions thereof such as pregelatinized starch, oxidized starch, ethylated starch, starch dextrins or maltodextrin, pectin, polysaccharides derived from seaweed such as agar, alginates, carrageenan, and fucellaran, seed gums such as guar gum and locust bean gum, polysaccharides derived from microbial fermentation such as xanthan gum and gellan gum, and nitrogen containing polysaccharides such as chitosan; or mixture of these.

In a particular embodiment, the polysaccharide is exudate gum polysaccharide such as gum Arabic, gum ghatti, gum karaya or gum tragacanth. A particular example of the polysaccharide is gum Arabic.

Gum Arabica is a natural gum collected as exudates from different species of Acacia trees (Fang et al. 2010 (2010) Biomolecules: 11, 1398-1405); a complex polysaccharide it has been used extensively in a wide range of industrial sectors including paint, glue, pharmaceuticals, textiles and food. Gum Arabic from the acacia tree is believed to be a branched polymer of galactose, rhamnose, arabinose, and glucuronic acid as the calcium, magnesium, and potassium salts with a mol. wt. of approx. 250,000. It has been shown (Badar, K. V. et al. (2011) Recent Research in Science and Technology 3 (5) 6-7) to have an effect on seed germination when seeds of certain plants are soaked in 1% solutions of gum arabica for 24 hours prior to germination. Futhermore, WO02/058466 reports that certain compositions comprising combinations of polysaccharides and peptides may increase crop yields.

The amount of polysaccharide administered to the plant wound should be sufficient to produce an enhanced nitrogen-fixing effect when in combination with the nitrogen-fixing bacteria and optionally also a surfactant. This will vary depending upon the various factors such as the particular polysaccharide used, the type of plant being treated, the nature of the wound, the particular strain of nitrogen-fixing bacteria employed and the method of administration. However, typically, a composition comprising from 0.1 to 1% w/w, for example from 0.1 to 0.5% w/w such as about 0.3% w/w polysaccharide is used.

In one embodiment, the composition comprises both a polysaccharide and an agriculturally acceptable surfactant. It has been found that, in some circumstances, these components enhance the effect of the nitrogen-fixing bacteria, and seem to work synergistically together to produce a more significant enhancement. Plants treated with a composition comprising these components may show increased growth as evidenced by increased dry weight of treated plants.

Novel compositions comprising the above-mentioned components form a further aspect of the invention. Thus in a further aspect the invention provides an agriculturally acceptable composition comprising a nitrogen-fixing bacteria, in particular *Gluconacetobacter diazotrophicus*, and a polysaccharide, a surfactant or a combination thereof.

The nitrogen-fixing bacteria are as described above, and in particular is *Gluconacetobacter diazotrophicus* are suitably present in the amounts described above. Similarly, the polysaccharide is a polysaccharide as described above, such as an exudate gum polysaccharide, for instance gum Arabic, and this is included in the composition in an amount as described above, for instance at a concentration of from 0.1 to 1% w/w polysaccharide. In addition the surfactant is suitably a surfactant as described above such as a non-ionic detergent, for instance surfactant that is 70% composed of the fatty acid oleic acid and the remainder a combination of linoleic, palmitic and stearic acids. In a particular embodiment, the composition will comprise from 0.0005 to 10% v/v surfactant for example from 0.0005 to 0.2% v/v surfactant.

In yet a further aspect, the invention provides a kit for preparing an agriculturally acceptable composition comprising a nitrogen-fixing bacteria. In such kits, the nitrogen-fixing bacteria, and in particular the *Gluconacetobacter diazotrophicus*, may be held separately from other components of the composition, for example in separate containers, or in a two-part pack or container. The nitrogen-fixing bacteria may be freeze-dried. The other components may be in the form of a concentrate, for ease of storage or transportation, ready for dilution with for example, water, at the point of use. Concentrates of this nature will contain the same components as the compositions listed above, but at generally higher levels. Thus, for example, a concentrate may contain from 1 to 10% w/w, for example from 1 to 5% w/w such as about 3% w/w polysaccharide, and a ten times dilution will result in the composition suitable for use in for example, the method of the invention. Similarly, the surfactant may be present in an amount of from 0.005 to 2% v/v in the concentrate. Other components, such as for example, a nutrient for the nitrogen-fixing bacteria is suitably including in the concentrate at the required concentration.

Kits of this type may be used to produce a composition of the invention, which may be used directly. In particular any concentrate will be diluted with water to an appropriate volume, whereupon the nitrogen-fixing bacteria will be added thereto.

The invention enables intracellular nitrogen fixation bacteria to be applied and delivered to a wide range of crops. In particular, these may be perennial, biennial or persistent annuals including but not limited to fruit trees and bushes (e.g. blueberries, raspberries and tea plants), vines, forage crops (alfalfa and grass for silage, hay or direct consumption by livestock) amenity grass and hedges, forestry, horticulture and herbs (e.g. chives, asparagus, eggplant).

It has previously been reported that Gd may improve production of sucrose-rich crops such as sugar beet or sugar cane (WO2010/022517). However, the applicants have found that using the treatment of the invention, improvement is seen in non-sucrose-rich crops and these form a particular embodiment of the invention.

In a particular embodiment, the method and composition of the invention is applied to grass such as amenity, turf or pasture grass, immediately or soon after mowing. This treatment leads to enhanced growth of the grass as is evident by an increase in dry weight of inoculated versus un-inoculated grass. It appears that the nitrogen-fixing bacteria are able to enter the grass through the wounds resulting from the mowing procedure, and colonise the grass plants intracellularly, leading to enhanced growth characteristics.

Furthermore, it has been found that colonization by Gd can increase the chlorophyll levels in plants and in particular in grass species such as pasture, amenity or turf grasses. As increase in chlorophyll is linked not only to nitrogen content but also to the level of greenness of the plants, this property is highly desirable in applications such as amenity grass where high levels of greenness are beneficial.

BRIEF DESCRIPTION OF THE DRAWINGS

Figure 1:
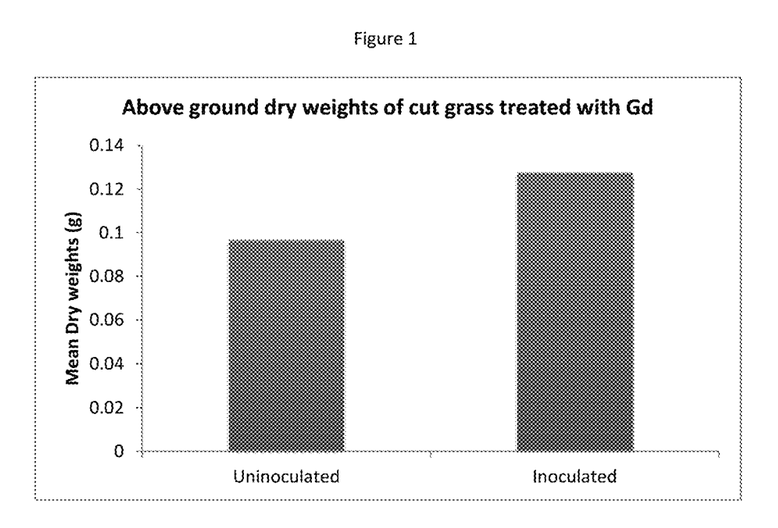
Figure 2:
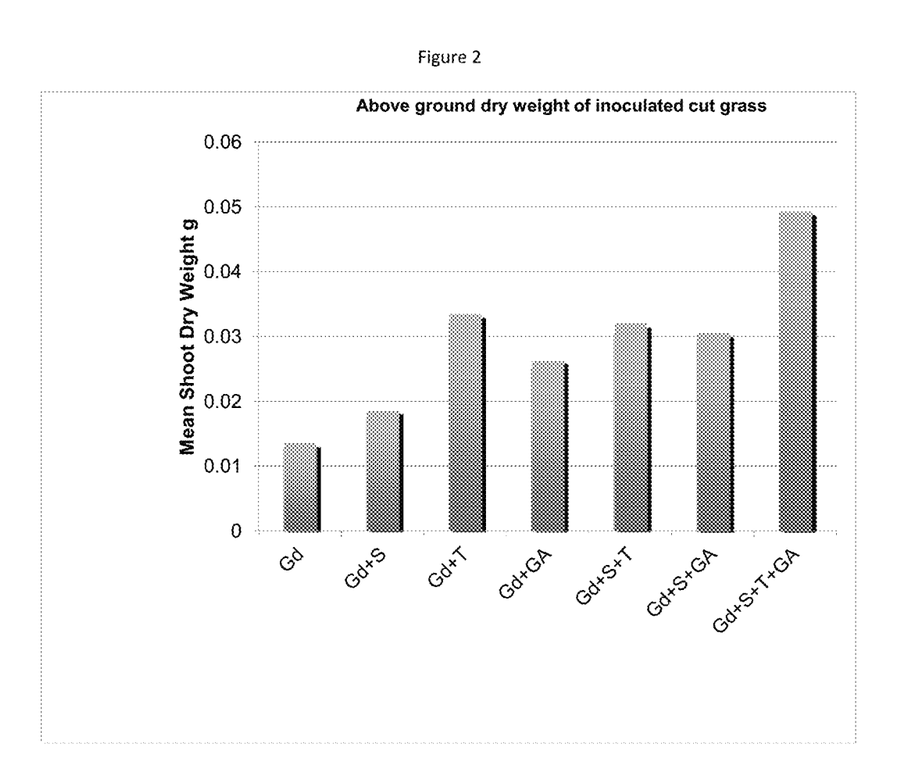
Figure 3A:
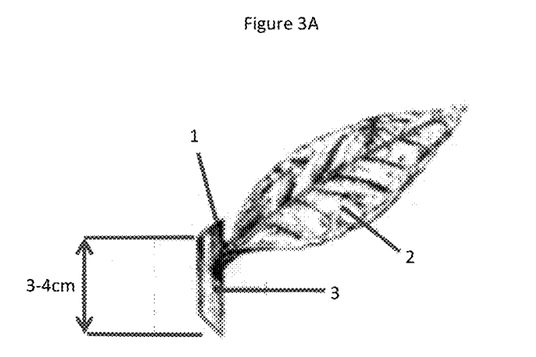
Figure 3B:
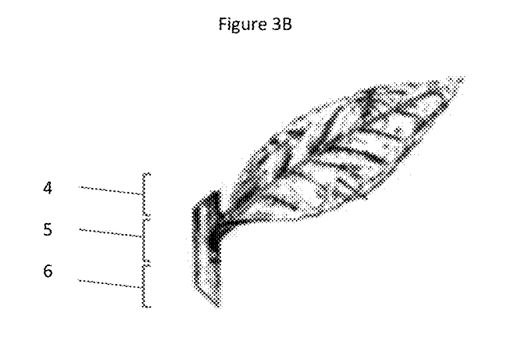
Figure 4:
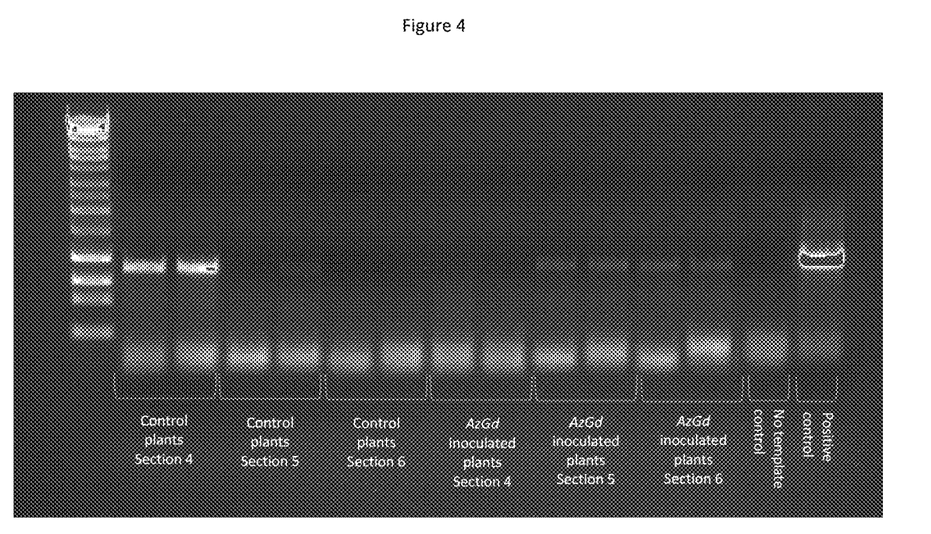
Figure 5:
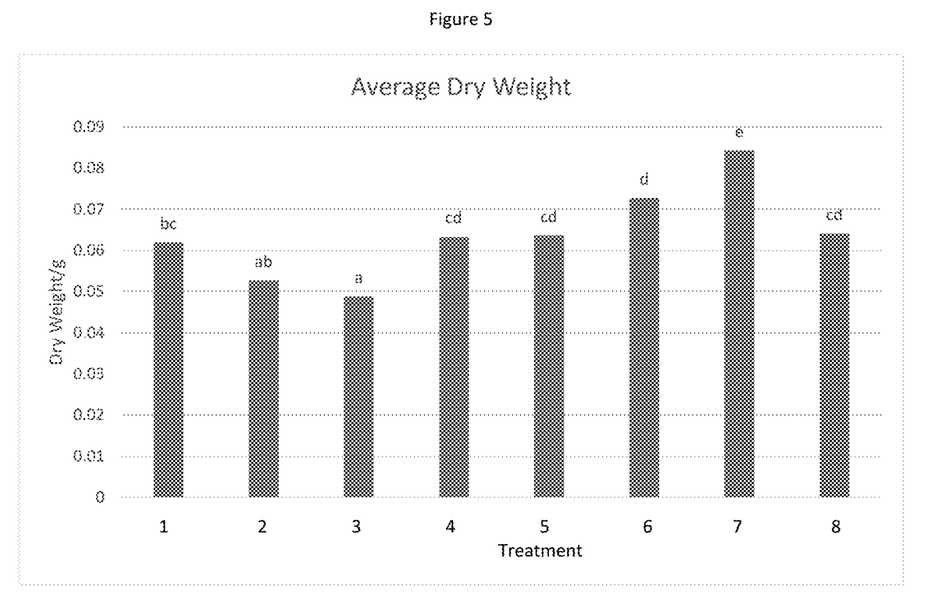
Figure 6:
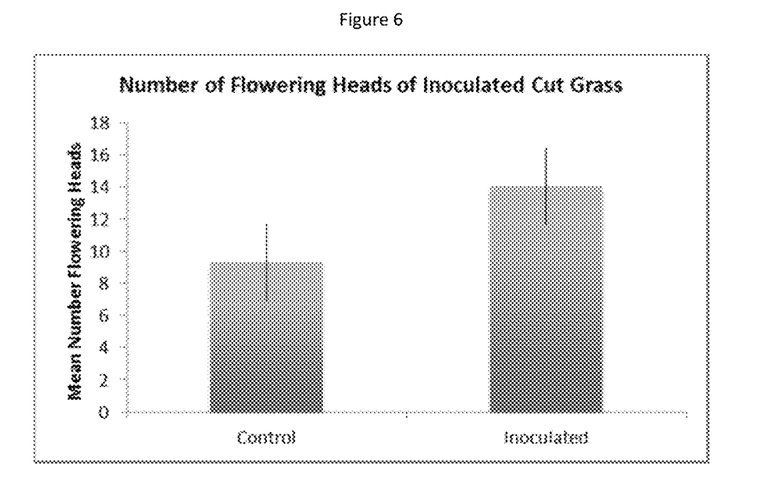
Figure 7:
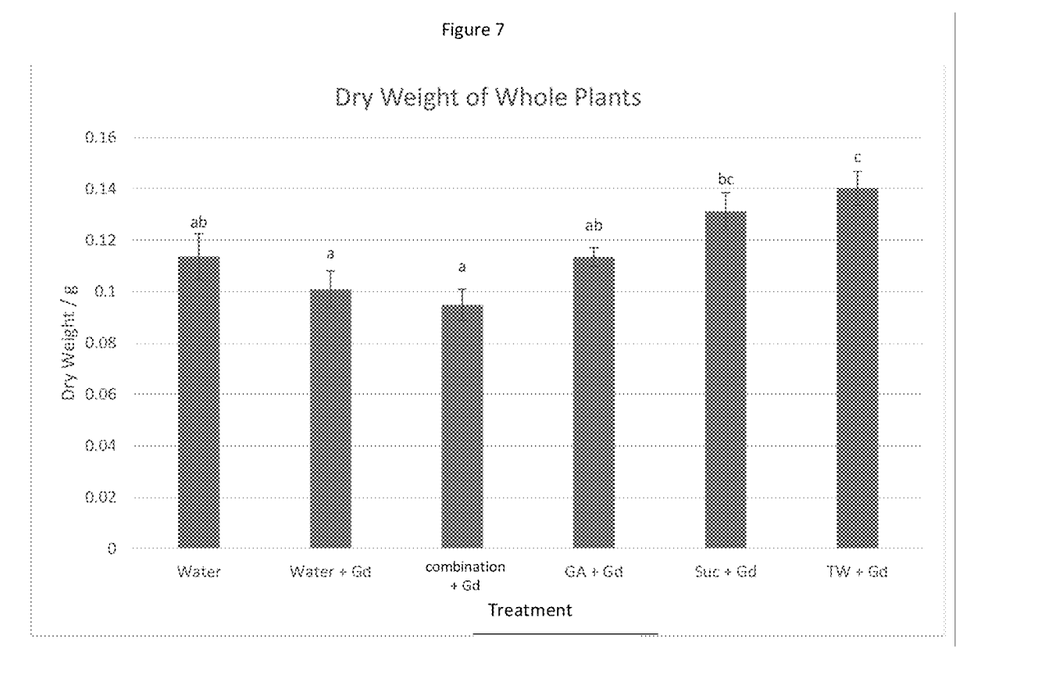

The invention will now be particularly described by way of example with reference to the accompanying diagrams in which:

FIG. 1 is a graph showing the mean dry weights (g) of un-inoculated and inoculated cut grass;

FIG. 2 is a graph showing the above ground dry weights of inoculated cut grass treated with Gd and sucrose, Tween and/or Gum Arabic or combinations thereof;

FIGS. 3A-3B illustrate an example of preparation of vegetative tea propagation, FIG. 3A illustrates the removal of the cutting; FIG. 3B is diagrammatical representation of sub-sections of each cutting taken for DNA isolation;

FIG. 4 shows an image of a gel of PCR products obtained from samples of tea plants which had been inoculated with Gd; all bands in control plants were sequenced and confirmed as non-specific binding. Sequenced bands from inoculated plants were confirmed as *Gluconacetobacter diazotrophicus*;

FIG. 5 is a graph showing the effects of various treatments on the biomass of cut grass;

FIG. 6 shows the results of a test to determine the effect of Gd on the number of flower heads of grass; and FIG. 7 is a graph showing the results of treatments with various compositions on the biomass of cut grass.

However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

EXAMPLE 1

Application to Cut Grass
Methodology
Culture of *G. diazotrophicus*:

*G. diazotrophicus* strain IMI 501986 (now IMI 504998) with the pRGS561 plasmid expressing GUS, were cultured on ATGUS medium, [0.8% (w/v) agar, yeast extract (2.7 g l$^{-1}$), glucose (2.7 g l$^{-1}$), mannitol (1.8 g l$^{-1}$), MES buffer (4.4 g l$^{-1}$), K$_2$HPO$_4$ (4.8 g l$^{-1}$), and KH$_2$PO$_4$ (0.65 g l$^{-1}$), pH 6.5] as required. Expression of the b-glucuronidase (gusA) gene was tested by plating on ATGUS medium containing X-Gluc (5-bromo-4-chloro-3-indolyl-beta-D -glucuronic acid cyclohexylammonium salt) at 50 mg l$^{-1}$; the formation of dark blue colonies indicated gusA gene expression.

Inoculation Procedures:

An aqueous suspension of the *G. diazotrophicus* was prepared to give an optical density at 600 nm of 1.1, c. 10$^9$ colony forming units (CFU) per milliliter. The number of 
CFU was determined by serial dilution, plating on ATGUS medium (with antibiotics as appropriate) and counting bacterial colonies after 4 d incubation in Petri dishes (28° C., dark). The suspension was diluted to $10^{-4}$ to produce a solution containing approximately 100 bacteria per ml ready for spraying as described below.

A standard weight of 0.5 g of grass *Lolium perenne* variety Cassiopeia seeds were sown in seedling trays of John Innes No. 1 compost and lightly covered with compost.

The individual trays were placed in larger trays and provided with adequate water in a growth room at 21° C./15° C. day/night 16/8 h cycle for 20 days. After which the grass was cut at a height of 2 cm above soil level using scissors (clippings were removed) and the following treatments were applied using a domestic handheld mist sprayer:

Experiment 1. Treatments
Control of water+3% sucrose
Gd+water+3% sucrose
Experiment 2 Treatments
Gd+water
Gd+water+3% sucrose
Gd+water+0.1% Tween
Gd+water+0.3% Gum Arabic
Gd+water+3% sucrose+0.1% Tween
Gd+water+3% sucrose+0.3% Gum Arabic
Gd+water+3% sucrose+0.1% Tween+0.3% Gum Arabic Dry Weight of Germinated Seedlings The seedlings were removed from the agar with forceps and all remaining agar washed from the roots. Each seedling was placed in a paper bag and placed in an oven 80° C. for 48 hours and then weighed.

Results from Experiments 1 and Experiment 2 are shown in FIGS. 1 and 2 respectively.

The results in FIG. 1 show a significant increase in the mean dry weight of the grass (0.09676 g for un-inoculated and 0.1276 g for inoculated graph). These dry weights were significantly different at $P<0.01$. Thus, inoculation in this manner clearly leads to a significant enhancement of growth.

These results shown in FIG. 2 show a significant difference ($P<0.001$) between Gd/S/T/GA and the next highest dry weight (Gd/T) and Gd/S/T, demonstrating a synergistic effect of the combinaton of three components. Gd and Gd/S are not significantly different at $P=0.05$.

EXAMPLE 2

Colonisation of Tea (*Camellia sinensis*) BY *Gluconacetobacter diazotrophicus* (*Azoticus*)

Vegetative Reproduction from a Stem Cutting

The standard means of vegetative propagation of tea clones is a single-leaf cutting. From larger stems comprising of approximately four to six nodes and a shoot tip, sections of stem and leaf were selected based upon health of the tissue (i.e. free of insects and diseases). The section chosen for the cutting was between red and green wood as recommended by Yamasaki et al. Soil and Crop Management, (2008) SCM-23). Recently matured shoots containing slightly reddened bark adjacent to mature leaves with actively breaking axillary buds have been found to result in the best rooting success.

From the preferred sections, a sample was selected comprising of a 3-5 cm section of stem and one healthy leaf. Each stem section was excised using a diagonal cut (1) approximately 0.5 cm above the leaf (2) and another diagonal cut below the leaf around an internode (3) avoiding pinching or bruising of the wound site (See FIG. 3A.)

The bottom of each tea stem cutting was dipped into 1% indole-butyric acid solution and placed into individual pots; the cutting planted with the stem straight of slightly slanted so that the leaf does not touch the soil. Each pot contained sand and John Innes number 1 cutting mix in a 4:1 ratio, saturated with water. To the cut top surface of each cutting either 20 μl of water, or 20 μl of Gd at $2.5\times10^5$ cfu/ml in water was applied, and the humidity of each sample maintained by covering each pot with a plastic sheet and sprayed lightly with water.

Following 3 months growth, and in order to confirm successful colonisation of the stem cuttings with Gd, uninoculated and inoculated stem cuttings were removed from the pots. Each cutting was sub-divided into sections which were (a) the top of shoot, including inoculation site (4) in (FIG. 3B), (b) the nodal section (5) in FIG. 3B, and (C) the lower stem section including any root tissue (6) in FIG. 3B. These sections where then snap frozen in liquid nitrogen.

DNA isolation from each section of cutting (i.e. 4, 5 and 6 in FIG. 3B) was carried out using TRIzol reagent according to the manufacturer's protocol and PCR performed. The PCR reaction carried out was a two-step reaction as described by Tian et. al., (2009); the first step using GDI-25F (5'-TAGTGGCGGACGGGTGAGTAACG-3'; SEQ ID NO:1) and GDI-923R (5'-CCTTGCGGGAAACAGCCATCTC-3'; SEQ ID NO:2) which amplified an 899bp product containing the amplicon of primers GDI139F (5'TGAGTAACGCGTAGGGATCTG-3'; SEQ ID NO:3) and GDI916R (5'-GGAAACAGCCATCTCTGACTG-3'; SEQ ID NO:4), the latter designed based upon 16S rDNA sequence information available in the GenBank database. After an initial denaturation step at 95° C. for 3 minutes, the following temperature profile was executed 32 times; denaturation for 20 seconds at 95° C., annealing for 45 seconds at 55° C., and extension for 20 seconds at 72° C., with a final extension step of 5 minutes at 72° C. One microliter of this PCR product was then taken and used as template for the second step of the PCR using GDI39F and GDI916R. Modifications to the parameters in the second round included increasing the annealing temperature to 62° C. for 15 seconds, and increasing the cycle number to 39. The PCR amplification products were analysed on a 1% agarose gel stained with ethidium bromide as well as sequenced to confirm identity of product (FIG. 4.).

Interestingly, AzGd was not detected in section 4 of the tea cutting suggesting that AzGd moved basipetally from the wound site following inoculation, being detected in sections 5 and 6 respectively.

Sequencing and subsequent BLAST results provided confirmation that the bands seen in section 4 of control plants were as a result of non-specific binding of the primer sets used, with the bands observed in sections 5 and 6 of inoculated tissue being identified as *Gluconacetobacter diazotrophicus* Pal5 (at 100% identification, 86% query cover and an E-value of 7e-04). The results suggest that AzGd although at a low copy number in the inoculated tissue did successfully colonise *Camellia sinensis* following inoculation of the wound site. This is possibly the first example of colonisation of a perennial plant by Gd.

EXAMPLE 3

Investigation of Effect of Treatment on Grass Biomass

Grass was grown in a plant growth chamber (Fitotron®) (23° C./15° C. at 65% humidity) in seed trays using John Innes No. 1 compost, for 2 weeks. It was then cut to a height of 8 cm and immediately sprayed with 10 ml of treatment as set out below using a domestic sprayer.

Treatments
1. Water
2. 3% sucrose+0.1% Tween+0.3% Gum Arabic
3. Water+Gd ($2.5\times10^5$ cfu/ml)
4. Water+3% sucrose+0.1% Tween+0.3% Gum Arabic+Gd ($2.5\times10^3$ cfu/ml)
5. Water+3% sucrose+0.1% Tween+0.3% Gum Arabic+Gd ($2.5\times10^4$ cfu/ml)
6. Water+3% sucrose+0.1% Tween+0.3% Gum Arabic+Gd ($2.5\times10^5$ cfu/ml)
7. Water+3% sucrose+0.1% Tween+0.3% Gum Arabic+Gd ($2.5\times10^6$ cfu/ml)
8. Water+3% sucrose+0.1% Tween+0.3% Gum Arabic+Gd ($2.5\times10^7$ cfu/ml)

The grass was returned to the Fitotron for a further 2 weeks under similar growth conditions. 5 plants, chosen at random, were cut at the soil level to form one sample and weighed. This was repeated a further five times to give six samples in total for each treatment.

These samples were dried in the oven for 48 hours and weighed.

The results are shown in FIG. 5. These results show that, provided some sucrose is present to support the growth of Gd, the biomass of the grass increased with the addition of Gd depending upon the formulation. Furthermore, the increase was dose dependent, with an optimum growth being observed at $2.5\times10^6$ cfu/ml. Such a dose may therefore be beneficial if the grass treated is pasture grass where maximising biomass is beneficial. However, if the grass treated is amenity or turf grass, lower biomass with enhanced greenness may be beneficial in that it may improve appearance without increasing the need for further cutting or mowing. In this case, a dosage of either less than or greater than $2.5\times10^6$ cfu/ml may be used.

EXAMPLE 4

Field Trial

A formulation comprising water+3% sucrose+0.1% Tween+0.3% gum Arabic+Gd ($2.5\times10^5$ cfu/ml) was applied to a single 1 $m^2$ cut grass plot (established Lolium perenne turf) relative to an 1 $m^2$ uninoculated cut grass plot treated with water only (control).

The formulation and water were applied, within 30 minutes of the grass being freshly mown, using a household mist sprayer to run-off. The control plot was protected from the treatment plot by a plastic screen. The application was made late afternoon in still air.

The 1 $m^2$ plots were subsampled using a 20 cm squared wire quadrant by counting the number of fully extended and fully formed flowering heads.

The results from each 20 cm square within each plot was averaged and the results are shown in FIG. 6. It is clear that the Gd treatment, applied in this way, substantially impacted on flower growth.

EXAMPLE 5

Comparison of Components of Composition

The method of Example 3 was repeated using various compositions including individual components of the composition used in that experiment. Specifically, the compositions used in this experiment were as follows:

Treatments

1. Water
2. Water+Gd ($2.5\times10^5$ cfu/ml)
3. Water+3% sucrose+0.1% Tween+0.3% Gum Arabic+Gd ($2.5\times10^5$ cfu/ml)
4. 0.3% Gum Arabic+Gd ($2.5\times10^5$ cfu/ml)
5. 3% Sucrose+Gd ($2.5\times10^5$ cfu/ml)
6. 0.1% Tween+Gd ($2.5\times10^5$ cfu/ml)

AberGlyn grass was grown for 2 weeks in John Innes No. 1 soil in a plant growth chamber (Fitotron®) at 23/15° C., 80% humidity. The grass was cut to a height of 8 cm with scissors, the cuttings removed and the grass immediately sprayed with the 10 ml treatment using a domestic sprayer. The grass was returned to plant growth chamber for a further two weeks.

Five plants were chosen at random from the tray and pooled together to make one sample and weighed. This was repeated a further five times so a total of six samples were taken per treatment. Grass was dried for 48 hours at 80° C. and then weighed.

The results are shown in FIG. 7. This experiment shows that the component used does have an effect on the growth of the grass. In this example, the surfactant gave the greatest increase in dry weight. Gum Arabic showed a marginal improvement only over the control, possibly due to the fact that the surfactant may be required to assist in the spread of the Gd on the plant and helps the liquid enter the wounds of the grass (although on this occasion, the combination did not show the expected an improvement). Again the water+Gd treatment was similar to the control so indicates that Gd needs the addition of at least some of these components to colonise the wounds.

The invention claimed is:

1. A method comprising wounding a growing plant above ground level in a preliminary step that does not involve introducing nitrogen-fixing bacteria to the plant and, subsequent to the preliminary step, administering nitrogen-fixing bacteria to a wound of the plant produced by wounding.

2. The method according to claim 1, wherein the wounding of the plant comprises wounding a stem or a leaf of the plant.

3. The method according to claim 1, wherein the wounding of the plant results from mowing, cutting, pruning, consumption by livestock, or harvesting.

4. The method according to claim 1, wherein the administering nitrogen-fixing bacteria to the plant is via a composition or a kit that, in addition to nitrogen-fixing bacteria, comprises a polysaccharide and/or a surfactant.

5. The method according to claim 4, wherein the polysaccharide is a hydrocolloid polysaccharide.

6. The method according to claim 4, wherein the polysaccharide is an exudate gum polysaccharide.

7. The method according to claim 1, wherein the administering nitrogen-fixing bacteria to the plant occurs from 1 to 48 hours after the wounding of the plant.

8. The method according claim 1, wherein the plant has an increased chlorophyll level relative to that of the plant prior to the method being applied to the plant.

9. The method according to claim 1, wherein the nitrogen-fixing bacteria comprise *Gluconacetobacter diazotrophicus*.

10. The method according to claim 1, wherein the nitrogen-fixing bacteria comprise a strain of *Gluconacetobacter diazotrophicus* deposited with CABI in the United Kingdom under the deposit accession number IMI 504998.

11. The method according to claim 1, wherein the nitrogen-fixing bacteria comprise a strain of *Gluconacetobacter diazotrophicus* deposited with CABI in the United Kingdom under the deposit accession number IMI 504958.

12. The method according to claim 1, wherein the nitrogen-fixing-bacteria provide the sole active component of a composition that is administered to the plant.

13. The method according to claim 1, wherein the plant is a perennial plant, a persistent annual plant, or a biennial plant.

14. The method according to claim 1, wherein the plant is an agricultural plant, a crop plant, a forestry plant, or a horticultural plant.

15. The method according to claim 1, wherein the plant is a fruit tree, a bush, a vine, a forage plant, an herb plant, or a grass plant.

16. The method according to claim 15, wherein the grass plant is an amenity grass plant, a pasture grass plant, or a turf grass plant.

17. A method for inoculating a plant with nitrogen-fixing bacteria, said method comprising, in a preliminary step, wounding a growing plant and thereafter administering nitrogen-fixing bacteria to a wound produced, wherein the plant is an amenity grass plant, a turf grass plant, or a pasture grass plant.

* * * * *